United States Patent [19]

Bryan et al.

[11] Patent Number: 5,709,887
[45] Date of Patent: Jan. 20, 1998

[54] METHOD AND COMPOSITION FOR TREATING TUMORS

[76] Inventors: Clifford R. Bryan, deceased, late of New Orleans, La.; by Marguerite Bryan, administratrix, 7310 Culpepper Dr., No. H, New Orleans, La. 70126

[21] Appl. No.: 466,435

[22] Filed: Jun. 6, 1995

[51] Int. Cl.$^6$ .......................... A61K 35/12; A61K 35/34; A61K 35/37; A61K 35/54

[52] U.S. Cl. .......................... 424/520; 424/548; 424/551; 424/582

[58] Field of Search .................. 424/520, 548, 424/551, 582

[56] References Cited

U.S. PATENT DOCUMENTS

| | | | |
|---|---|---|---|
| 5,002,071 | 3/1991 | Harrell | 428/897 |
| 5,208,022 | 5/1993 | Eggers | 424/194.1 |

FOREIGN PATENT DOCUMENTS 59-134728  2/1984  Japan ................ A61K 35/23

*Primary Examiner*—John W. Rollins
*Attorney, Agent, or Firm*—Browdy and Neimark

[57] ABSTRACT

A biological is used as a therapeutic agent or booster to produce sustained responses in the immune cells against tumors. The biological of the present invention is derived from the pleuroperitoneal organs of a neotenic amphibian, e.g., axolotl, or from the notochord and surrounding tissues of an Agnathan, e.g., Lamprey eel, or from mesenteries and visceral organs from the pleuroperitoneal cavity of older fetuses or baby vertebrates from fish to humans, or from tadpoles of frogs at the stage when both the tail and the four legs are present, i.e., just before completion of the metamorphosis period.

21 Claims, No Drawings

METHOD AND COMPOSITION FOR TREATING TUMORS

FIELD OF THE INVENTION

The present invention is directed to a method and composition for prophylaxis and treatment of tumors in humans.

BACKGROUND OF THE INVENTION

The immune system is capable of identifying microorganisms and chemical toxins as foreign. This ability prevents us from falling prey to the same infection over and over again. The immune system of Man and most vertebrates can recognize "self" (syngeneic tissue) and distinguish it from "others" (allogeneic tissue). The immune system also has the potential to recognize abnormal tissue or "altered self" and destroy it in order to remove dead or dying tissue, or aberrant cells. That potential could be utilized to teach the immune system how to reject cancer, (Boon, T. "Teaching the immune system to fight cancer," *Scientific American*, March 1993; 82–89).

Knowledge of the cellular basis of the immune system has permitted us to prevent many of the serious diseases of the past, such as small pox, measles, and tetanus. Cancer, on the other hand, continues to be a major challenge to most scientists. Unlike microbial infections and toxins, cancer cells are not foreign to the body. They are syngeneic. Cancer cells are altered or aberrant cells. They may have cancer specific antigens which allows us to recognize these cells in vitro or have altered appearances which permit the observer to recognize them under the microscope. But these alterations do not appear to stimulate the immune system sufficiently to eliminate or destroy them. The body appears to require additional antigenic stimulation to handle the cancerous tumor.

Immunity to tumors is thought to depend on a specific white cell called a lymphocyte, (Herberman, R B., "Tumor immunology[Review]," *JAMA*, 1992; 268(20):2935–9). There are three different types of white cells: the phagocyte, monocyte, and lymphocyte cells. The phagocyte and the monocyte cells form the body's first line of defense. They engulf and digest bacteria, fungi and viruses that invade the body. The third type of white cell, the lymphocyte, is the body's memory cell. It protects the host from invading organisms that the body has no natural immunity to. The lymphocytes can be divided into two distinct populations: T-cells and B-cells. Both are probably derived in the embryo from bone marrow stem cells. However, the T-cell is pre-processed in the thymus gland before going to the bone marrow and lymph nodes. The T-cells are responsible for killing invading organisms and regulating the immune response.

The B-cells are responsible for making antibodies. They are called B-cells because this population of cells was first described in birds and the pre-processing occurs in the bursa of Fabricius. The bursa is not found in mammals and there is no certainty as to where B-lymphocytes are pre-processed, but many investigators believe that it is in the bone marrow. It is known that B-lymphocytes are responsible for antibody production and thus humoral immunity.

Humoral immunity is the term used to describe the immune functions performed by liquid substances found in the serum, saliva, tears and stomach secretions, that assist the phagocytes in recognizing foreign substances. Antibodies are chemical substances which combine with antigens. Antibodies can be divided into four major classes: I-gM, I-gG, I-gA and I-gE. I-gM is a large molecule, or macroglobulin. It represents the first response to either immunization or infection. It peaks during the first 7 days following infection. It is usually found only in the serum. I-gG is the second immunoglobulin formed in response to either immunization or infection. It peaks around 21 days following infection. It has a lower molecular weight than I-gM. It can be found in tissues throughout the body as well as in serum. It is produced in large quantities following booster immunizations. I-gA is found in saliva, sweat, and tears. I-gE is produced in response to allergy producing antigens.

Other components of the human immune system are the complements which assist phagocytic cells in recognizing microorganisms as foreign. The antibodies produced by the B-cells are well recognized. However, there are fluid substances that are produced by T-lymphocytes—lymphokines—which include Interleukin (Il-2). Lymphokines are thought to help the T-cells in many regulating functions, including the killing of tumors and microorganisms.

The T-cell is the cytotoxic killer of the acquired immune system and thought to be the major aggressor involved in destroying both cancer cells and viruses. However, studies indicate that a totally intact immune system is required for optimal destruction and the T-cell alone cannot take sole credit for inhibiting tumor growth, (Herberman, R B., "Tumor immunology[Review]," *JAMA*, 1992;268(20):2935–9). Natural killer cells may potentially be involved in tumor killing, and macrophage (tissue monocytes) play an important role as well. Macrophages are phagocytes that process antigens and present them to the B-cell in a form that enhances immunoglobulin production.

Despite advances in diagnostic techniques and some advances in treatment of tumors, there is still a great lack of understanding of the causes and treatment of most cancer.

The most widely recognized characteristic feature of cancer is its rapid growth, which rivals the growth of fetal tissues. However, unlike fetal tissues, tumor cells show scant regard for the biological precision and orderliness of mitosis and other growth phenomena associated with normal tissues.

In addition to its erratic mitotic behavior, cancer shows a complete lack of harmony and cooperation in its relation with neighboring tissues, frequently impinging on their rightful place, robbing the normal tissues of nutrients, and a host of other aggressive acts.

Another well known fact about cancer is its affinity for the old. Although people of all ages have been victimized by cancer, the old are much more vulnerable to cancer than the young. If one lives to a ripe old age, one's chances of getting cancer are greatly enhanced. Older patients are known to have a blunted immune response as compared to younger patients. The immune system is the security guard that monitors the body, seeking out abnormal clones. As the immune system ages, its ability to detect and reject abnormal clones decreases.

Rejection of transplanted tissue is well enough understood to permit grafting of allogeneic tissue from a source other than the host. However, when dealing with cancer, which is syngeneic tissue (i.e., same as the host), our knowledge is limited. Tissue transplants have become routine. Transplant grafts in many respects exhibit a pattern similar to cancer. Like cancer, these grafts are surrounded by tissues with which they are unfamiliar and often find hostile. The host often rejects the graft, in the absence of immune-suppressing medication. However, most tumors are not rejected. The important difference between grafts and tumors is the immunogenicity. While the graft engenders a potent antibody response, cancer engenders only minimal antibody response. When antitumor antibody is produced by the host, this antibody is usually not cytotoxic.

Metastasis is the phenomenon in which cancer cells from a primary site are thought to break loose from the original tumor and are transported by the circulatory or lymphatic system and then lodge in other organs. Once firmly entrenched, the cells manifest all the behavioral characteristics of the cells in the primary site.

Although it is quite evident that metastases occur, there is some evidence that in many cases which were previously thought to represent metastatic tumors are, in fact, two independently arising tumors that occur simultaneously, e.g. retinoblastoma. The discovery of one before the other does not make one primary and the other a secondary metastasis.

In 1866 Ernst Haeckel, in his Biogenetic Law concerning Recapitulation stated, "Ontogeny recapitulates phylogeny", which in essence refers to the fact that an organism during its developmental stages passes through several of the stages found in the developmental stages of its ancestors. As an illustration, human fetuses at certain stages of development possess notochord, neural tubes, gills, tubular hearts, tails, etc. These structures have little or no function that we know of in the fetuses, and are not present in a human at birth. The same is true for other mammals, reptiles, birds, amphibians, and fish.

What is not always readily apparent is that the astounding resemblance of the gross anatomy of fetuses of the vertebrate classes portends a deep and fundamental resemblance of thousands of micro-structures which even embraces chemical resemblance if not identity.

The present applicant believes that the maturation process of the fetus holds important clues needed to control cancer. The etiology of cancer may be due to the absence of cell products which trigger maturation and differentiation on one hand, or due to the failure of the immune surveillance response, which recognizes abnormal pre-cancer cells and destroys them.

The present invention recognizes the fact that during ontogeny of humans, as well as other vertebrates, a large number of compounds are produced by the genes and elaborated by the cells in order to produce the orderly growth exhibited by the fetus.

It has been reported by some observers that fetal antigens have been frequently found in the serum of cancer patients, and have even been found in association with malignant growths. The best known examples of this are:

1. The alpha-feto protein found in the serum of normal pregnant females, as well as some patients with liver and ovarian tumors, and found on other tumors containing fetal tissue; and 2. CEA-carcinoembryonic antigen found in colon cancer.

It should also be noted that the immune system has several functions, four of which are:

1. Controlling the cellular products of genes by destroying them and removing them from the system;

2. Breaking down and digesting all worn out or impaired current cells and eliminating their unused parts;

3. Acting as the body's main line of defense against parasites which have entered the body parenterally, such as bacteria, viruses, fungi and worms;

4. Destruction of tumors mediated by the T-cell system.

Presently, either surgery, radiation, or chemotherapy are used for treating tumors. All of these techniques have disadvantages. For example, chemotherapy is toxic to normal cells as well as to cancer cells, and radiation affects not just the cancer cells but the adjacent tissues as well. Surgery also has attendant disadvantages and dangers to the patient.

Harrell, in U.S. Pat. No. 5,002,071, discloses using material from a human placenta to augment soft tissue. In this case, however, the invention is limited to human tissue and does not anticipate an immune response; it is merely used to increase the amount of soft tissue for, e.g., plastic surgery.

Eggers, U.S. Pat. No. 5,208,022, discloses a vaccine composition for inducing anti-tumor immunity comprising of syngeneic non-malignant cells coupled with adjuvant compounds. These non-malignant cells are derived from fibroblasts, kidney fibroblasts, epithelial cell lines and lymphoid cells which are mixed in solution or covalently coupled to an adjuvant, preferably an adjuvant peptide. Eggers uses syngeneic cell lines to stimulate the immune system, whereas the present invention used xenogeneic tissue (different species).

Seiji, in Japanese Publication No. 59-134728, discloses an immunocancer agent containing as an active ingredient water-soluble or water-dispersible protein and glucoprotein separated from living cell membranes in internal organs of mammalian fetuses. In this case the materials are derived solely from mammalian fetuses, blood, blood vessels, connective tissues and lipid tissues. Blood and blood vessels are first removed and the remainder is homogenized in an isotonic solution with their cells by grinding them. Seiji uses only mammalian tissue and totally different processing of tissue from the present invention. The present invention utilizes amphibian tissue and fetuses of other vertebrates.

SUMMARY OF THE INVENTION

It is an object of the present invention to provide a biological treatment for tumors.

It is another object of the present invention to provide a prophylactic biological for treatment of tumors.

It is a further object of the present invention to provide a method for making such a biological.

It is another object of the present invention to provide a therapy which has the potential for extending the survival of the tumor patient without altering the quality of the patient's life.

It is now known that in most normal individuals there are often malignant or abnormal clones of cells that arise spontaneously. The immune system is generally capable of eliminating these abnormal clones. However, with advancing age, many individuals lose their ability to destroy these malignant clones.

After about age fifty, the immune system appears to lose some of its tumor surveillance mechanism. We know that the thymus atrophies with age, and there is a significant loss of thymic hormone levels which may contribute in some way to the observed loss of tumor surveillance function of the immune system. The therapy and prophylaxis of the present invention is based upon the assumption and belief that the immune cells may have lost their memory or ability to destroy tumors related to embryonic antigens.

Immunization has long been used to protect against disease and to restore the memory of immune cells for diseases such as smallpox, measles, polio, typhoid, etc. These immunizations may protect for a limited time, and often require booster injections to maintain a protective level of immunity. Following boosters, the cells regain their memory and produce antibodies at levels even higher than before.

In accordance with the present invention, the biological of the present invention is used as a therapeutic agent or booster to produce sustained responses in the immune cells against the tumors. The biological of the present invention is derived from the pleuroperitoneal organs of a neotenic amphibian, e.g., axolotl, or from the notochord and surrounding tissues of an Agnathan, e.g., Lamprey eel, or from mesenteries and visceral organs from the pleuroperitoneal cavity of older fetuses or baby vertebrates from fish to humans, or from tadpoles of frogs at the stage when both the tail and the four legs are present, i.e., just before completion of the metamorphosis period.

More specifically, the present invention provides a biological, i.e., a composition, for treatment and prophylaxis of tumors comprising a suspension or homogenate prepared from organs and tissues selected from the group consisting of pleuroperitoneal organs of a neotenic amphibian, the notochord and surrounding tissues of agnathan, the mesenteries and visceral organs from the pleuroperitoneal cavity of fetuses and baby vertebrates, and from tadpoles of frogs at the stage when both the tail and four legs are present. Specific amphibians include necturus or axolotl.

The composition of the present invention is obtained by harvesting organs selected from the group consisting of pleuroperitoneal organs of a neotenic amphibian and amphibian larvae, the notochord and surrounding tissues of an agnathan, the mesenteries and visceral organs from the pleuroperitoneal cavity of fetuses and baby vertebrates, and from tadpoles of frogs at the stage when both the tail and four legs are present; and suspending the cells from the organs in medium for tissue culture. Alternatively, the harvested organs may be mechanically subdivided prior to being introduced into the medium, such as by homogenization.

In preparing the composition, the organs may be subdivided by manual dissection with scissors and the tissues teased apart prior in medium, or the organs may be homogenized. Dimethylsulfoxide and freezing may be used to preserve the suspension or homogenate.

Studies were conducted using an experimentally induced tumor, L1210 leukemia, in $BDF_1$ susceptible mice. L1210 was chosen because it is a standard tumor used for screening anticancer agents, and one skilled in the art would expect that agents which are useful in treating animals with L1210 leukemia would be useful in treating human cancer patients. The active composition was derived from visceral organs from the pleuroperitoneal cavity of the larvae of neotenic amphibians, axolotls. The process of obtaining the active ingredient according to the present invention is unique because it uses tissue suspension and homogenate from neotenic amphibian larvae, not merely early embryonic tissues, to inhibit tumor growth.

DETAILED DESCRIPTION OF THE INVENTION

The active ingredient of the present invention is a biological derived from the mesenteries and/or visceral organs from the pleuroperitoneal cavity of neotenic amphibians, such as necturus or axolotl. The biological is irradiated with 7500 rads administered in three fractions of 2500 rads each. The 7500 rads are sufficient to sterilize the biological and inactivate both T-cells and macrophage. RPMI (Roswell Park Memorial Institute) medium for tissue culture was added at the rate of 10 ml per gram of tissue, and then the mixture was mechanically blended to a smooth homogeneous consistency. Although RPMI was used, normal saline or other isotonic solution can be used. RPMI was chosen because it is an ideal medium for freezing.

One method of manufacturing the biological for treatment and prophylaxis of tumors comprises the following steps:

A. Treatment—Suspension

1. The animals, larvae axolotl, were etherized.
2. The animals' skins were prepped with Betadyne and then rinsed three times with sterile distilled water and rinsed once with RPMI medium for tissue culture solution.
3. Each animal was dissected with an initial incision at diaphragm level. The lungs and other contents of the pleuroperitoneal cavity, with the exception of the gut (intestines) and blood vessels, were carefully removed with scissors to reduce contamination with blood. The tissue was teased apart with fine dissecting scissors.
4. The tissues harvested were weighed, and suspended in tissue culture medium at the rate of 10 grams of tissue/100 ml RPMI medium.
5. The mixture of suspension tissue and tissue culture medium was irradiated at 7500 rads with three fractionated doses or 2500 rad each.
6. Half the suspension solution of 50 ml was further diluted 1:1 to 100 ml with RPMI and prepared for preservation.
7. Preservation was effected by using 10% freezing solution containing dimethyl sulfoxide (DMSO) and cooling to −70° C. in a Reevco freezer. To prepare the freezing solution, 10 ml. of DMSO was slowly added to 90 ml. RPMI on ice to cool the solution from the exothermic reaction caused by the addition of DMSO.
8. The unpreserved mixture was used for initial injections, and was injected intraperitoneally at 0.4 cc per injection into the mice.
9. A total of five doses of the biological were administered in three day intervals.
10. During administration of the biological, the animals were observed for anaphylaxis and anaphylactic precautions were taken. However, no anaphylaxis was observed.

B. Treatment—Homogenate

1. The animals, larvae axolotl, were etherized.
2. The animals' skin was prepped with Betadyne and then rinsed three times with distilled water and once with RPMI solution.
3. Each animal was dissected at the diaphragm, and the lungs and other contents of the pleuroperitoneal cavity with the exception of the gut(intestines) and blood vessels, were removed to make a cell homogenate.
4. The harvested tissues were weighed, and a tissue homogenate was prepared from 15 grams of tissue per 100 ml RPMI. The tissue was homogenized using a Waring blender for 30 seconds. The homogenate was decanted to remove larger pieces of cellular debris.
5. The homogenate solution is 15 grams of tissue per 100 ml RPMI diluted 1 to 3.
6. The homogenate solution was then further diluted with RPMI to a final concentration of 0.0005 mg/ml.
7. Preservation was effected using irradiation as above, and then freezing both with DMSO and without DMSO.
8. The dosage to each mouse treated was 0.4 cc of homogenate per treatment, with a total of five treatments at three day intervals.
9. The resulting biological had a smooth, homogeneous consistency. The biological can be administered as an intraperitoneal or intramuscular injection as a booster to produce an anti-tumor response.
10. During administration of the booster, the animals were observed for anaphylaxis and anaphylactic precautions were taken. However, no anaphylaxis was observed.

The biological of the present invention was tested in a number of experimental studies. Tables I and II show the results of tests which were conducted on a number of control groups of mice of the $BDF_1$ strain and which compare survival experiences using the Lee-Desu statistic.

Table I, based upon administration of a suspension of the biological, demonstrates that the survival time of mice treated in accordance with the claimed invention was greater than the survival time of the control group.

Table II, based upon administration of the homogenate of the biological to the treatment group subjects, further confirms the increase of survival rate using the biological of the present invention.

TABLE 1

COMPARISON OF SURVIVAL EXPERIENCE USING THE LEE-DESU STATISTIC
(32 DAYS INTERVAL AFTER CANCER INJECTION)
A. Treatment-suspension Group Compared with the Control Group
(Cancer Without Treatment)

| Group | Total N | Uncensored | Censored | % Censored | Meanscore | Median Survival Time (Days) |
|---|---|---|---|---|---|---|
| 1. Control Group (Cancer Without Treatment) | 12 | 11 | 1 | 8.33 | −7.2500 | 28.0 |
| 2. Treatment Suspension Group (Cancer, plus Suspension Treatment) | 12 | 4 | 8 | 66.67 | 7.2500 | 32.0+ |

Pairwise comparison Statistic 6.673, D.F. = 1, Prob. = 0.01

TABLE II

COMPARISON OF SURVIVAL EXPERIENCE USING THE LEE-DESU STATISTIC
(32 DAYS INTERVAL AFTER CANCER INJECTION)
B. Treatment-Homogenate Group Compared with the Control Group
(Cancer without Treatment)

| Group | Total N | Uncensored | Censored | % Censored | Meanscore | Median Survival Time (Days) |
|---|---|---|---|---|---|---|
| 1. Control Group (Cancer Without Treatment) | 12 | 11 | 1 | 8.33 | −5.6667 | 28.0 |
| 2. Treatment Homogenate Group (Cancer, plus Homogenate Treatment) | 12 | 5 | 7 | 58.33 | 5.6667 | 32.0+ |

Pairwise comparison Statistic 4.016, D.F. = 1, Prob. = 0.04

As can readily be seen from the two tables above, the biological of the present invention significantly prolonged the survival of susceptible mice which had been injected with L1210 leukemia, the standard tumor used by the National Cancer Institute to evaluate new chemotherapeutic drugs. This leukemia is rapidly fatal in susceptible strains of mice like BDF1, and statistically significant prolongation of life clearly indicates the efficacy of the treatment.

Similarly, when used as a prophylactic, the biological of the present invention demonstrates efficacy. As a prophylactic, five doses of the treatment were administered to the mice at three day intervals. The interval between treatment with the prophylaxis and injection of tumor was between 28 and 34 days. This time was chosen because it permitted full activation of the immune system including both primary and secondary immune responses. Then the leukemia was injected into the experimental and the control mice. The results of these studies are presented in Tables III and IV. Both the homogenate and suspension treatments prolonged life in the control group.

TABLE III

COMPARISON OF SURVIVAL EXPERIENCE USING THE LEE-DESU STATISTIC
(35 DAYS INTERVAL AFTER CANCER INJECTION)
C. Prophylactic-Suspension Group Compared with the Control Group
(Cancer Without Prophylactic)

| Group | Total N | Uncensored | Censored | % Censored | Meanscore | Median Survival Time (Days) |
|---|---|---|---|---|---|---|
| 1. Control Group (Cancer Without Treatment) | 13 | 12 | 1 | 7.69 | −6.2308 | 27.83 |
| 2. Prophylactic Suspension Group (Suspension Treatment, Then Cancer) | 11 | 5 | 6 | 54.55 | 7.3636 | 38.50 |

Pairwise comparison statistic 5.673, D.F. = 1, Prob. = 0.02

TABLE IV

COMPARISON OF SURVIVAL EXPERIENCE USING THE LEE-DESU STATISTIC
(35 DAYS INTERVAL AFTER CANCER INJECTION)
D. Prophylactic Homogenate Group Compared with the Control Group
(Cancer Without Prophylactic)

| Group | Total N | Uncensored | Censored | % Censored | Meanscore | Median Survival Time (Days) |
|---|---|---|---|---|---|---|
| 1. Control Group (Cancer Without Treatment) | 13 | 12 | 1 | 7.69 | −5 | 27.83 |
| 2. Prophylactic Homogenate Group (Homogenate Treatment, then cancer) | 12 | 7 | 5 | 41.67 | 5.4167 | 34 |

Pairwise comparison statistic 3.199, D.F. = 1, Prob. = 0.07
*Without freezing solution The term "treating" means the administering to subjects a biological according to the present invention for purposes which can include prevention, amelioration, or cure of a tumor or malignancy.

Medicaments are considered to be provided "in combination" with one another if they are provided to the patient concurrently or if the time between the administration of each medicament is such as to permit an overlap of biological activity.

In one preferred embodiment, at least one biological according to the present invention comprises a single pharmaceutical composition.

Pharmaceutical compositions for administration according to the present invention can comprise at least one biological according to the present invention in a pharmaceutically acceptable form optionally combined with a pharmaceutically acceptable carrier. These compositions can be administered by any means that achieve their intended purposes. Amounts and regiments for the administration of a biological according to the present invention can be determined readily by those with ordinary skill in the clinical art of treating cancers.

For example, administration can be by parenteral, such as subcutaneous, intravenous, intramuscular, intraperitoneal, transdermal, or buccal routes. Alternatively, or concurrently, administration can be by the oral route. The dosage administered depends upon the age, health and weight of the recipient, type of previous or concurrent treatment, if any, frequency of treatment, and the nature of the effect desired.

Compositions within the scope of this invention include all compositions comprising at least one biological according to the present invention in an amount effective to achieve its intended purpose. While individual needs vary, determination of optimal ranges of effective amounts of each component is within the skill of the art. Typical dosages comprise about 0.1 to about 100 mg/kg body weight. The preferred dosages comprise about 1 to about 100 mg/kg body weight of the active ingredient. The most preferred dosages comprise about 10 to about 100 mg/kg body weight.

Therapeutic administration can also include prior, concurrent, subsequent or adjunctive administration of at least one additional biological according to the present invention or other therapeutic agent, such as an immune stimulating agent. In such an approach, the dosage of the second drug can preferably be the same as or different from the dosage of the first therapeutic agent. Preferably, the drugs are administered on alternate days in the recommended amounts of each drug.

Administration of a biological of the present invention can also optionally include previous, concurrent, subsequent or adjunctive therapy using immune system boosters or immunomodulators. In addition to the pharmacologically active compounds, a pharmaceutical composition of the present invention can also contain suitable pharmaceutically acceptable carriers comprising of excipients and auxiliaries which facilitate processing of the active compounds into preparations which can be used pharmaceutically. Preferably, the preparations, particularly those preparations which can be administered orally and which can be used for the preferred type of administration, such as tablets, dragees, troches and capsules, and also preparations which can be administered rectally, such as suppositories, as well as suitable solutions for administration by injection or orally, contain from about 0.01 to 99 percent, preferably from about 20 to 75 percent of active compound(s), together with the excipient.

Pharmaceutical preparations of the present invention are manufactured in a manner which is itself known, for example, by means of conventional mixing, granulating, dragee-making, dissolving, or lyophilizing processes. Thus, pharmaceutical preparations for oral use can be obtained by combining the active compounds with solid excipients, optionally grinding the resulting mixture, and processing the mixture of granules, after adding suitable auxiliaries, if desired or necessary, to obtain tablets or dragee cores.

Suitable excipients are, e.g., fillers such as saccharide, for example, lactose or sucrose, mannitol or sorbitol; cellulose preparations, zinc compounds and calcium phosphates, such as tricalcium phosphate or calcium hydrogen phosphate; as well as binders such as starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents can be added such as the above-mentioned starches and also carboxymethyl starch, cross-linked polyvinyl pyrrolidone, agar, or algininc acid or a salt thereof, such as sodium alginate. Auxiliaries are, above all, flow-regulating agents and lubricants, for example, silica, talc, stearic acid or salts thereof, such as magnesium stearate or calcium stearate, and/or polyethylene glycol. Dragee cores are provided with suitable coatings which, if desired, are resistant to gastric juices. For this purpose, concentrated saccharide solutions can be used, which can optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropylmethyl cellulose phthalate are used. Dyestuffs or pigments can be added to the tablets or dragee coatings, for example, for identification or in order to characterize combinations of active compound doses.

Other pharmaceutical preparations which an be used orally include push-fit capsules made of gelatin, as well as soft, sealed capsules made of gelatin and a plasticizer such as glycerol or sorbitol. The push-fit capsules can contain the active compounds in the form of granules which can be mixed with fillers such as lactose, binders such as starches, and/or lubricants such as talc or magnesium stearate and, optionally, stabilizers. In soft capsules, the active compounds are preferably dissolved or suspended in suitable liquids, such as fatty oils or liquid paraffin. In addition, stabilizers can be added.

Possible pharmaceutical preparations which can be used rectally include, for example, enemas and/or suppositories which consist of a combination of the active compounds with a suppository base. Suitable suppository bases are, for example, natural or synthetic triglycerides, or paraffin hydrocarbons. In addition, it is also possible to use gelatin rectal capsules which consist of a combination of the active compounds with a base. Possible base materials include, for example, liquid triglycerides, polyethylene glycols, or paraffin hydrocarbons.

Suitable formulations for parenteral administration include aqueous solutions of the active compounds in water-soluble form, for example, water-soluble salts such as normal saline or zinc solutions. In addition, suspensions of the active compounds as appropriate oily injection suspensions can be administered. Suitable lipophilic solvents or vehicles include fatty oils, such as sesame oil, or synthetic fatty acid esters, such as ethyl oleate or triglycerides. Aqueous injection suspensions that can contain substances which increase the viscosity of the suspension include, for example, sodium carboxymethyl cellulose, sorbitol, and/or dextran. Optionally, the suspension can also contain stabilizers.

Pharmaceutical formulations for systemic administration according to the invention can be formulated for enteral, parenteral or topical administration. Indeed, all three types of formulation can be used simultaneously to achieve systemic administration of the active ingredient.

Suitable formulations for oral administration include hard or soft gelatin capsules, dragees, troches, pills, tablets, including coated tablets, elixirs, suspensions, syrups or inhalations and controlled release forms thereof.

Solid dosage forms in addition to those formulated for oral administration include rectal suppositories.

The biologicals of the present invention can also be administered in the form of an implant when compounded with a biodegradable slow-release carrier. Alternatively, the biological of the present invention can be formulated as a transdermal patch for continuous release of the active ingredient.

Suitable formulations for topical administration include creams, gels, jellies, mucilages, pastes and ointments. Suitable injectable solutions include intravenous subcutaneous and intramuscular injectable solutions. Alternatively, the biologicals may be administered in the form of an infusion solution or as a nasal inhalation or spray.

The foregoing description of the specific embodiments will so fully reveal the general nature of the invention that others can, by applying current knowledge, readily modify and/or adapt for various application such specific embodiments without departing from the generic concept, and therefore such adaptations and modifications are intended to be comprehended within the meaning and range of equivalents of the disclosed embodiments. It is to be understood that the phraseology or terminology herein is for the purpose of description and not of limitation.

All references cited in this specification are hereby incorporated by reference.

What is claimed is:

1. A composition for treatment or preventing recurrence of tumors comprising a suspension containing at least one active ingredient obtained from the pleuroperitoneal organs of an amphibian or larva of an amphibian, from the notochord and surrounding tissues of an Agnathan, or from mesenteries and visceral organs from the pleuroperitoneal cavity of fish or tadpoles of frogs at the stage when both the tail and the four legs are present;

wherein said active ingredient is obtained by harvesting tissues obtained from the pleuroperitoneal organs of an amphibian or a larva of an amphibian, or obtained from the notochord and surrounding tissues of an Agnathan or from mesenteries and visceral organs from the pleuroperitoneal cavity of fish or tadpoles of frogs at the stage when both the tail and four legs are present;

subdividing said organs to form a suspension; and placing said suspension in tissue culture medium.

2. The composition according to claim 1 wherein the amphibian is axolotl or necturus.

3. The composition according to claim 1 wherein the active ingredient is obtained from an amphibian or an amphibian larva.

4. A method for treating tumors comprising administering an effective amount of the composition according to claim 1 to a patient suffering from tumors.

5. A method for preventing recurrence of tumors in a patient comprising administering an effective amount of the composition according to claim 1 to said patient.

6. A composition for treatment or preventing recurrence of tumors comprising a homogenate containing at least one active ingredient obtained from the pleuroperitoneal organs of an amphibian or a larva of an amphibian, from the notochord and surrounding tissues of an Agnathan, or from mesenteries and visceral organs from the pleuroperitoneal cavity of fish or tadpoles of frogs at the stage when both the tail and the four legs are present;

wherein said active ingredient is obtained by harvesting tissues obtained from the pleuroperitoneal organs of an amphibian or a larva of an amphibian, or obtained from the notochord and surrounding tissues of an Agnathan or from mesenteries and visceral organs from the pleuroperitoneal cavity of fish or tadpoles of frogs at the stage when both the tail and four legs are present;

subdividing said organs into a homogenate; and placing said homogenate into tissue culture medium.

7. The composition according to claim 6 wherein the amphibian is axolotl or necturus.

8. The composition according to claim 6 wherein the active ingredient is obtained from an amphibian or an amphibian larva.

9. A method for treating tumors comprising administering an effective amount of the composition according to claim 6 to a patient suffering from tumors.

10. A method for preventing recurrence of tumors in a patient comprising administering an effective amount of the composition according to claim 6 to said patient.

11. A method for preparing a composition for treatment and preventing recurrence of tumors comprising:

harvesting tissues obtained from the pleuroperitoneal organs of an amphibian or larva of an amphibian, from the notochord and surrounding tissues of an Agnathan, or from mesenteries and visceral organs from the pleuroperitoneal cavity of fish or tadpoles of frogs at the stage when both the tail and the four legs are present;

mincing said organs; and suspending the minced organs in tissue culture solution to form a suspension.

12. The method according to claim 11 wherein said tissues are submerged in tissue culture medium and are subdivided by manual dissection with scissors to tease tissues apart to release cells to provide a cell suspension.

13. The method according to claim 11 wherein the suspension is preserved by adding dimethyl sulfoxide and freezing the suspension.

14. The method according to claim 11 wherein the suspension is irradiated to sterilize the suspension.

15. The method according to claim 14, wherein the suspension is irradiated with 7500 rads administered in three doses of 2500 rads each.

16. A method for preparing a composition for treatment and prophylaxis of tumors comprising:

(a) harvesting tissues obtained from the pleuroperitoneal organs of an amphibian or a larva of an amphibian, or obtained from the notochord and surrounding tissues of an Agnathan or from mesenteries and visceral organs from the pleuroperitoneal cavity of fish or tadpoles of frogs at the stage when both the tail and four legs are present;

(b) dividing said organs into a homogenate; and (c) adding said homogenate to tissue culture medium to form said composition.

17. The method according to claim 16 wherein said tissues are submerged in tissue culture medium in step (b) for being subdivided to form a homogenate.

18. The method according to claim 17 wherein dimethyl sulfoxide is added or not added, to the composition prior to freezing.

19. The method according to claim 16 wherein the homogenate is irradiated to sterilize the homogenate.

20. The method according to claim 19 wherein the homogenate is irradiated with 7500 rads administered in three doses of 2500 rads each.

21. The method according to claim 16 wherein the composition is preserved by freezing the composition.

* * * * *